(12) United States Patent
Horn et al.

(10) Patent No.: US 7,943,221 B2
(45) Date of Patent: May 17, 2011

(54) HINGED COMPLIANCE FIBER BRAID BALLOON

(75) Inventors: Daniel J. Horn, Shoreview, MN (US); John J. Chen, Plymouth, MN (US); Aaron Khieu, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1220 days.

(21) Appl. No.: 11/438,564

(22) Filed: May 22, 2006

(65) Prior Publication Data

US 2007/0267128 A1    Nov. 22, 2007

(51) Int. Cl.
B29D 22/00 (2006.01)
B29D 23/00 (2006.01)
B32B 1/08 (2006.01)

(52) U.S. Cl. .......... 428/36.91; 428/35.7; 428/36.4; 428/36.1; 428/36.2; 606/192; 604/103.13

(58) Field of Classification Search .......... 428/35.7, 428/36.1, 36.2, 34.1, 36.4, 36.91; 606/192; 604/103.13
See application file for complete search history.

(56) References Cited

U.S. PATENT DOCUMENTS

| | | | |
|---|---|---|---|
| 4,702,252 A | 10/1987 | Brooks et al. | |
| 4,706,670 A | 11/1987 | Anderson et al. | 128/344 |
| 4,896,669 A | 1/1990 | Bhatte et al. | 606/194 |
| 4,906,244 A | 3/1990 | Pinchuk et al. | 606/194 |
| 4,935,190 A | 6/1990 | Tennerstedt | 264/529 |
| 4,950,239 A | 8/1990 | Gahara et al. | 604/96 |
| 4,963,313 A | 10/1990 | Noddin et al. | 264/573 |
| 5,026,607 A | 6/1991 | Kiezulas | 428/423.7 |
| 5,096,848 A | 3/1992 | Kawamura | 437/67 |
| 5,135,516 A | 8/1992 | Sahatjian et al. | 604/265 |
| 5,201,706 A | 4/1993 | Noguchi et al. | 604/96 |
| 5,250,069 A | 10/1993 | Nobuyoshi et al. | 606/192 |
| 5,270,086 A | 12/1993 | Hamlin | 428/35.2 |
| 5,304,121 A | 4/1994 | Sahatjian | 604/53 |
| 5,304,340 A | 4/1994 | Downey | 264/521 |
| 5,306,246 A | 4/1994 | Sahatjian et al. | 604/96 |
| 5,328,468 A | 7/1994 | Kaneko et al. | 604/96 |
| 5,330,428 A | 7/1994 | Wang et al. | 604/96 |
| 5,330,429 A | 7/1994 | Noguchi et al. | 604/96 |
| 5,338,299 A | 8/1994 | Barlow | 604/96 |

(Continued)

FOREIGN PATENT DOCUMENTS

EP    540858    9/1992

(Continued)

OTHER PUBLICATIONS

U.S. Appl. No. 11/407,576, filed Apr. 20, 2006, Khieu, Aaron, et al.

*Primary Examiner* — Michael C Miggins
(74) *Attorney, Agent, or Firm* — Vidas, Arrett & Steinkraus

(57) ABSTRACT

Composite fiber reinforced balloons for medical devices are prepared by applying a web of fibers to the exterior of a preformed underlayer balloon which has been pressurized and expanded to a predetermined pressure or above ambient size, encasing the web with a matrix material to form an assembly with the fiber web bonded to the underlayer balloon. The assembly may have an outer layer formed by inserting the assembly into a preformed outer layer balloon. The overlayer balloon can be bonded to the assembly during a heat set step.

17 Claims, 5 Drawing Sheets

U.S. PATENT DOCUMENTS

| | | | |
|---|---|---|---|
| 5,344,400 A | 9/1994 | Kaneko et al. | 604/96 |
| 5,348,538 A | 9/1994 | Wang et al. | |
| 5,403,340 A | 4/1995 | Wang et al. | 606/194 |
| 5,500,180 A | 3/1996 | Anderson et al. | 264/532 |
| 5,503,631 A | 4/1996 | Onishi et al. | 604/96 |
| 5,509,899 A | 4/1996 | Fan et al. | 604/96 |
| 5,556,383 A | 9/1996 | Wang et al. | 604/96 |
| 5,576,072 A | 11/1996 | Hostettler et al. | 427/532 |
| 5,578,374 A | 11/1996 | Dunbar et al. | 428/364 |
| 5,647,848 A | 7/1997 | Jorgensen | 604/96 |
| 5,693,034 A | 12/1997 | Buscemi et al. | 604/265 |
| 5,702,754 A | 12/1997 | Zhong | 427/2.12 |
| 5,702,756 A | 12/1997 | McKean et al. | 427/127 |
| 5,714,110 A | 2/1998 | Wang et al. | 264/529 |
| 5,797,877 A | 8/1998 | Hamilton et al. | 604/96 |
| 5,827,289 A | 10/1998 | Reiley et al. | 606/86 |
| 5,833,657 A | 11/1998 | Reinhardt et al. | 604/96 |
| 5,958,582 A | 9/1999 | Dunbar et al. | 428/364 |
| 6,110,483 A | 8/2000 | Whitbourne et al. | 424/423 |
| 6,146,356 A | 11/2000 | Wang et al. | 204/96 |
| 6,156,254 A | 12/2000 | Andrews et al. | 264/531 |
| 6,270,522 B1 | 8/2001 | Simhambhatla et al. | 623/1.11 |
| 6,528,150 B2 | 3/2003 | Nazarova et al. | 428/212 |
| 6,572,813 B1 | 6/2003 | Zhang et al. | 264/519 |
| 6,673,053 B2 | 1/2004 | Wang et al. | 604/265 |
| 6,723,267 B2 | 4/2004 | Simmelink et al. | 264/203 |
| 6,746,425 B1 | 6/2004 | Beckham | |
| 6,977,103 B2 | 12/2005 | Chen et al. | 428/37.7 |
| 2002/0049402 A1 | 4/2002 | Peacock, III et al. | |
| 2003/0143350 A1 | 7/2003 | Jimenez et al. | 428/35.2 |
| 2004/0082965 A1 | 4/2004 | Beckham | 606/192 |
| 2004/0109964 A1 | 6/2004 | Beckham | 428/35.9 |
| 2005/0015046 A1 | 1/2005 | Weber et al. | 604/96.01 |
| 2005/0123702 A1 | 6/2005 | Beckham | 428/36.3 |
| 2005/0271844 A1 | 12/2005 | Mapes et al. | |
| 2006/0008606 A1 | 1/2006 | Horn et al. | 428/36.1 |
| 2006/0085023 A1 | 4/2006 | Davies, Jr. et al. | |
| 2006/0085024 A1* | 4/2006 | Pepper et al. | 606/192 |
| 2007/0250101 A1 | 10/2007 | Horn et al. | |

FOREIGN PATENT DOCUMENTS

| | | |
|---|---|---|
| EP | 0 553 960 | 8/1997 |
| WO | WO98/03218 | 1/1998 |
| WO | 98/05377 | 2/1998 |
| WO | 2005/072804 | 8/2005 |
| WO | 2006/016934 | 2/2006 |
| WO | 2006/086516 | 8/2006 |
| WO | 2007/037821 | 4/2007 |

* cited by examiner

HINGED COMPLIANCE FIBER BRAID BALLOON

BACKGROUND OF THE INVENTION

Medical devices comprising catheter shafts and catheter balloons are used in an increasingly widening variety of applications including vascular dilatation, stent delivery, drug delivery, delivery and operation of sensors and surgical devices such as blades, and the like. The desired physical property profile for the balloons used in these devices varies according to the specific application, but for many applications a high strength robust balloon is necessary and good softness and trackability properties are highly desirable.

Commercial high strength balloons having wall strengths in excess of 20,000 psi have been formed of a wide variety of polymeric materials, including PET, nylons, polyurethanes and various block copolymer thermoplastic elastomers. A particular application which has a very high pressure requirement is reopening of stenoses which develop at or in long-term shunt, ports or grafts employed for repeated blood access, for instance with dialysis patients. Such stenoses are often highly calcified and essentially must be subjected to very high pressure for successful treatment. Moreover, frequently the vessels into which the access devices are connected are quite large. Consequently there is a need for balloons whose pressure profile allows for use of pressures in excess of 20 atm at balloon diameters which can exceed 5 mm.

Documents relating to fiber reinforced medical balloons include U.S. Pat. No. 4,896,669, Behate; U.S. Pat. No. 4,706,670, Andersen; U.S. Pat. No. 5,647,848, Jorgensen; U.S. Pat. No. 5,201,706, and U.S. Pat. No. 5,330,429, Noguchi; U.S. Pat. No. 5,827,289, Reiley; and U.S. Pat. No. 6,156,254, Andrews.

In commonly owned copending application U.S. application Ser. No. 10/889,574, filed Jul. 7, 2004, published as US 2006-0008606 A1, published Jan. 12, 2006, high strength composite fiber reinforced balloons for medical devices are described. Such balloons are prepared by applying a web of fibers to the exterior of a preformed underlying balloon and encasing the web with a matrix material to form a composite balloon. The fiber web is applied to at least the cone portion of the underlying balloon form. Either the cone portion of the underlying balloon form, or the web fibers applied to said cone portion, or both, have a friction-enhancing material coated thereon.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

The invention pertains to fiber reinforced laminate composite balloons and processes for preparing laminate composite balloons. Some aspects the present invention may pertain to modifications of the invention of US 2006-0008606 A1. Other aspects of the invention pertain more generally to composite fiber reinforced medical device balloons.

In some aspects, the invention pertains to fiber reinforced laminate composite balloons and processes for preparing laminate composite balloons that exhibit hinged compliance curves upon expansion. In one such aspect, the balloon comprises a polymer material underlayer, an overlying fiber web adhered to the underlayer and a layer of matrix material either covering the fiber web or encasing it. In some aspects of the invention, the matrix material and fiber web are covered by an overlayer balloon.

In preparing the composite balloons of the present invention, an underlayer balloon is formed and expanded to a predetermined pressure such that its diameter is increased from its nominal diameter. While the underlayer balloon is expanded at the predetermined pressure, the fiber web is applied over at least a portion of the underlayer balloon. The fiber web may cover the cone portions and/or the body portion of the underlayer balloon. The fiber web is bonded to the underlayer balloon with a suitable adhesive. The fiber web is then covered or encased in a matrix material. The balloon assembly additionally may be inserted into an outerlayer balloon forming a composite balloon. The composite balloon may then be heat set to bond the layers together. The composite balloon is then deflated and assembled onto a catheter shaft and wrapped and sterilized.

In an alternative embodiment the size of the underlayer balloon is monitored as pressure is increased until a predetermined size, above the nominal size, is reached. Application of the fiber web and matrix material are as described above.

In some aspects the invention pertains to manufacturing processes for preparing composite fiber reinforced balloons. One such aspect the method comprises:

providing a preformed underlayer balloon having a size at ambient pressure;

expanding the preformed underlayer balloon by pressurizing the underlayer balloon to a predetermined pressure above ambient, or until it reaches a predetermined size above the ambient pressure size; and while the underlayer balloon remains pressurized:

applying a web of fibers to the exterior of said underlayer balloon;

adhering the web of fibers to the underlayer balloon; and encasing the web with a matrix material to form an assembly of underlayer balloon and fiber matrix.

In particular embodiments of this aspect of the invention, after the matrix material has been applied an overlayer balloon may be applied to the assembly of underlayer balloon, fiber web and matrix material and bonded thereto, for instance by heat activation of the matrix material.

As noted above, some aspects of the invention are directed to balloons that exhibit hinged compliance curves. That is, in measuring and plotting the growth of the diameter of the composite balloon over an increase in internal pressure in a first pressure range, the balloon has a compliance curve which has a first slope and in a second pressure range, which is higher than the first pressure range, the balloon has a compliance curve which has a second slope which is less then the first slope. The hinge point of the hinged compliance curve is taken as the point of intersection between the first and second slopes. The resulting balloon is less compliant at the higher pressures of the second pressure range than it is at the lower pressures of the first pressure range.

In one inventive aspect, the balloon comprises an underlying balloon layer, a fiber web disposed over the underlying balloon layer, a matrix material encasing the web and an overlying balloon layer of radially oriented polymer material disposed over the fiber web and matrix material wherein the balloon exhibits a hinged compliance curve.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

DETAILED DESCRIPTION OF THE INVENTION

Figure 1:
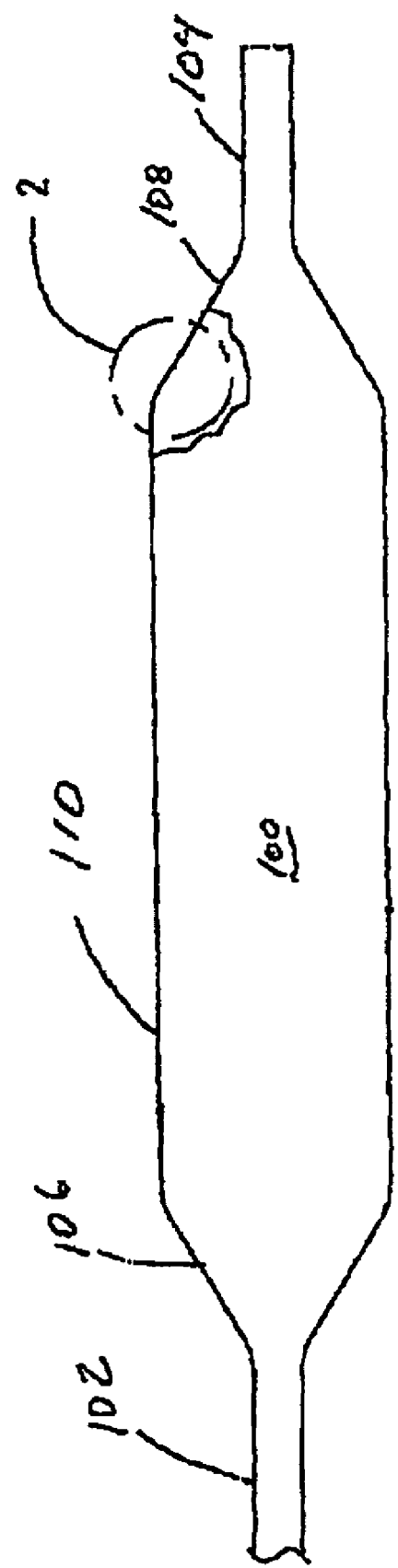
FIG. 1 is a schematic side view of an underlayer balloon with a partial cutaway.

All US patents and applications and all other published documents mentioned anywhere in this application are incorporated herein by reference in their entirety.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Balloons of the invention are particularly suited to use in medical devices, for instance on balloon angioplasty catheters, in stent delivery systems, perfusion balloon devices, cutting balloon devices, cryoplasty devices, and the like. Typically they will be mounted on a catheter or probe device.

Referring to the drawing FIGS. 1-5, several aspects of the inventive processes are illustrated.

Figure 2:
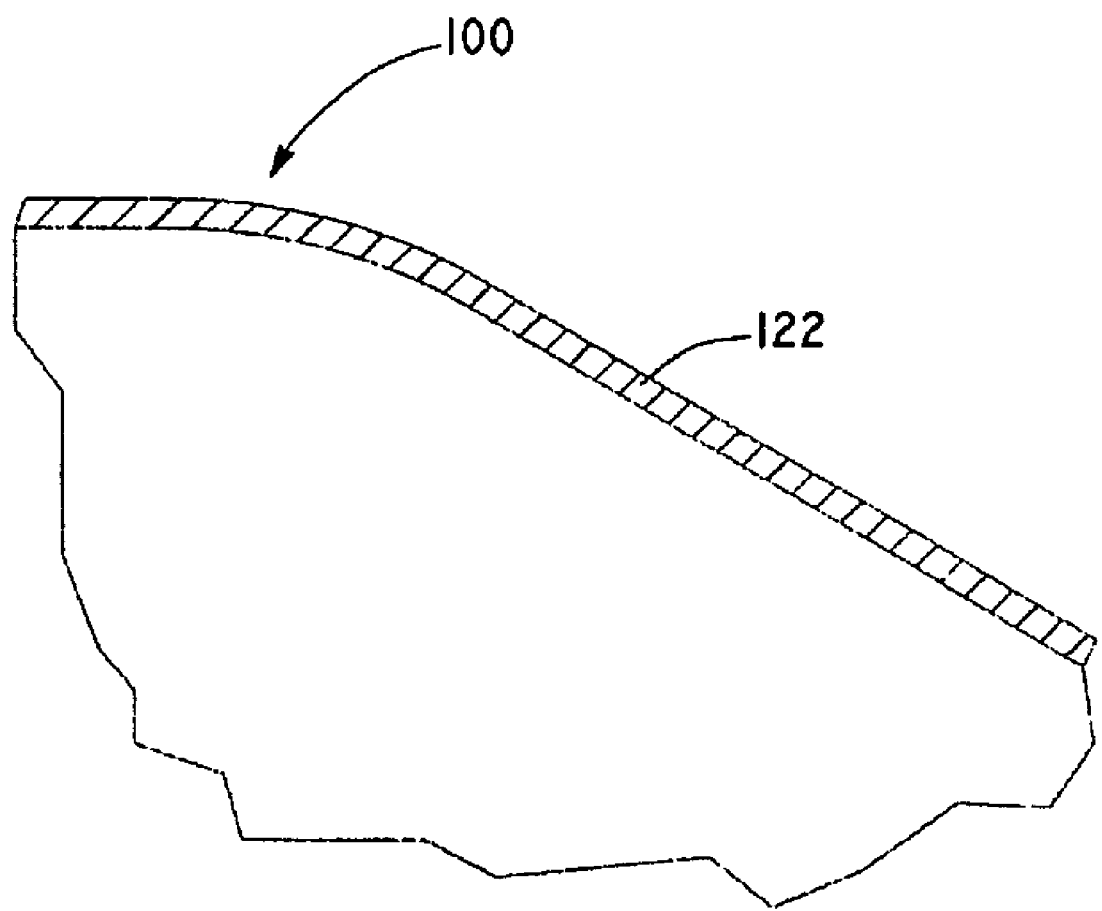
FIG. 2 is an enlarged cutaway view taken at line 2 of FIG. 1.

FIGS. 1 and 2 show an underlayer balloon 100 comprising waist regions 102, 104, cone regions 106, 108 and body region 110. The underlayer balloon 100 may be formed of a single layer 122 polymer material, for instance of a radially oriented thermoplastic polymer. As will be further addressed below, before commencing with the remaining additions of material onto the underlayer balloon 100, the underlayer balloon 100 is pressurized and expanded to a predetermined pressure above ambient or equivalently to a predetermined size above its size at ambient pressure.

Figure 3:
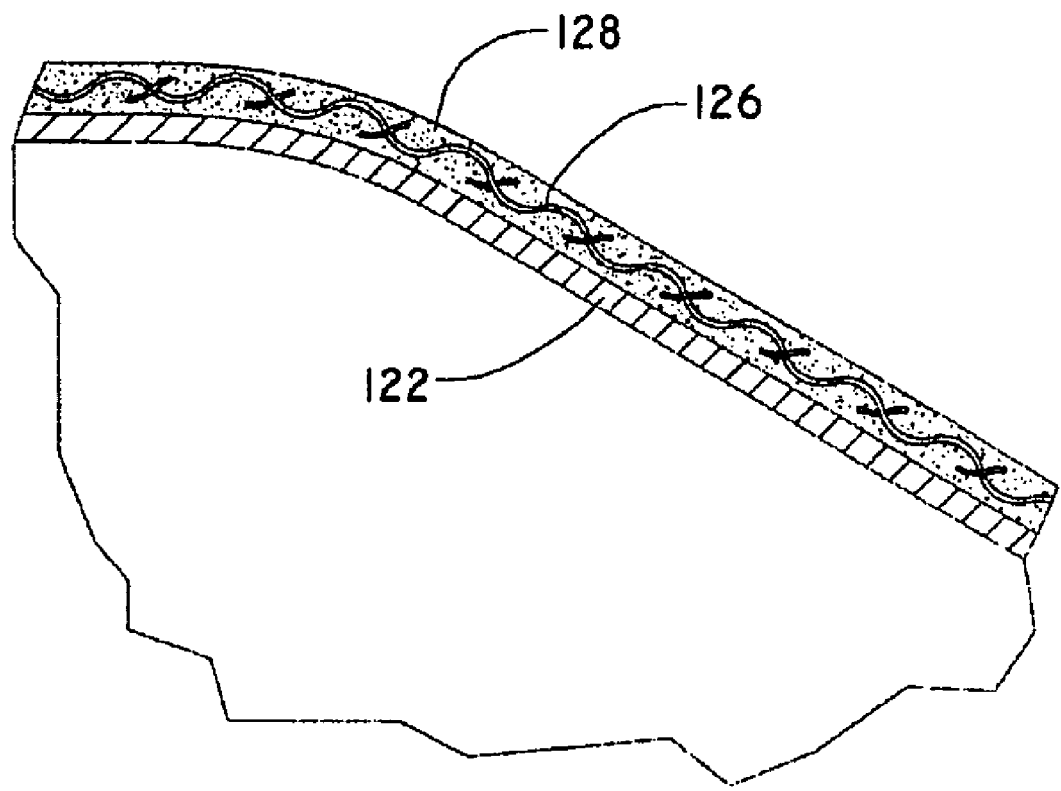
FIGS. 3 and 4 are views as in FIG. 2 illustrating steps of an embodiment of the inventive method.

FIG. 3 is a view as in FIG. 2, after application of a fiber web 126 and matrix material 128. The fiber web 126 is encased by the matrix material 128.

Figure 4:
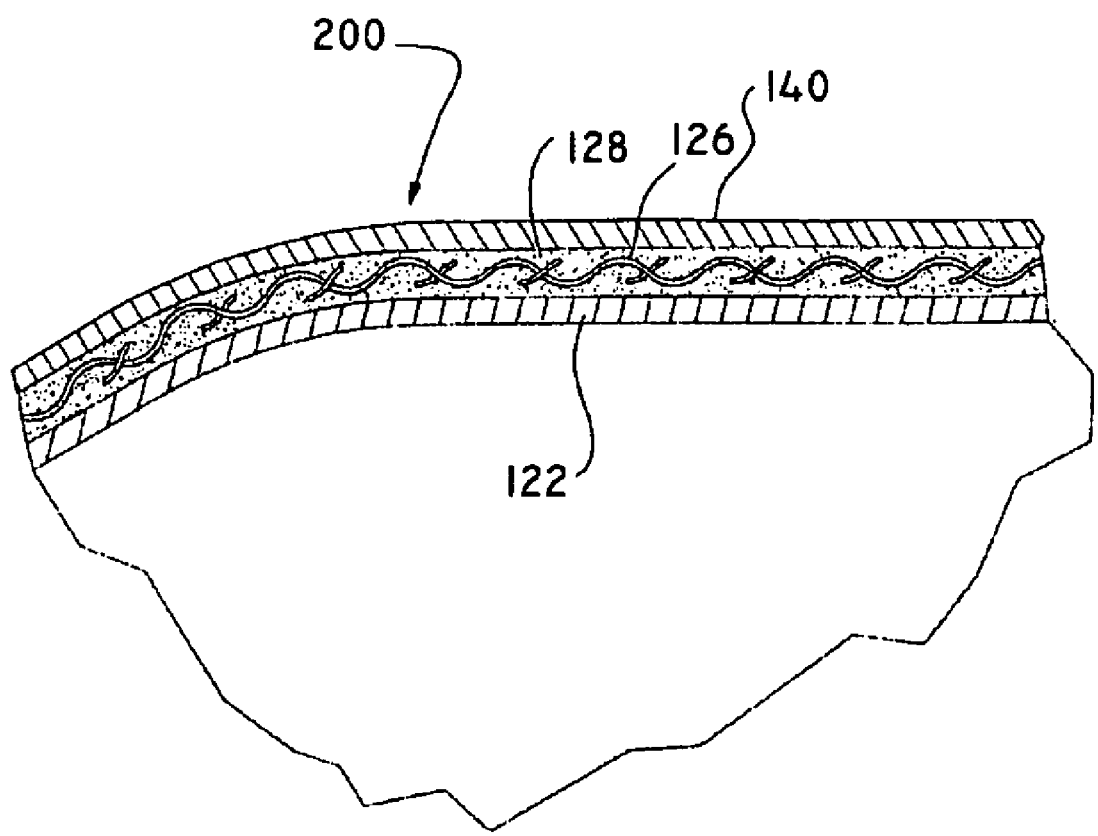

FIG. 4 is a view as in FIG. 3, after the application of an outerlayer balloon 140 to complete the composite balloon 200. The matrix material 128 and fiber web 126 are sandwiched between layer 122 provided by the underlayer balloon and the layer 140 provided by the outerlayer balloon.

Figure 5:
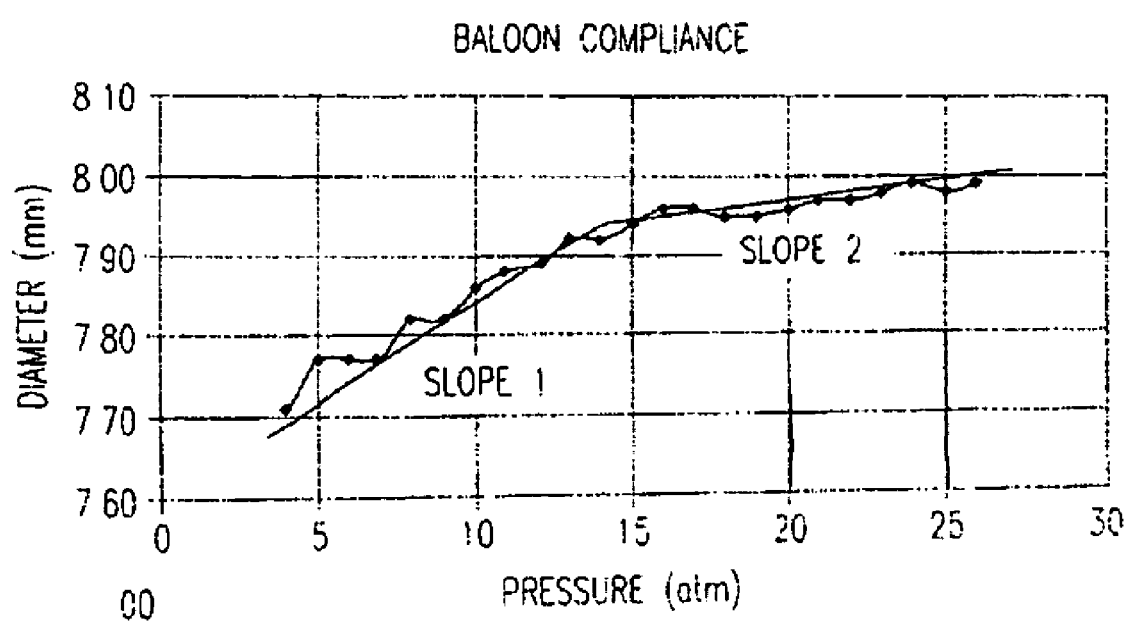
FIG. 5 is a graph of the distension from nominal diameter to burst of a composite balloon of the invention.

FIG. 5 is a graph of the distension from nominal diameter to burst of a composite balloon of the invention. The curve represents the increase in diameter of the composite balloon over a particular pressure range. The curve shown indicates a hinged compliance. This is a profile in which the balloon initially grows at a relatively rapid rate but at higher pressures grows more slowly.

The initial slope segment labeled slope 1 and the diameter of the intersection of slopes 1 and the final slope segment labeled slope 2 in the graph can be adjusted by changing the inflation pressure of the underlayer balloon 100 during the braiding process. The hinge point 220, i.e. the intersection point of slope 1 and slope 2, may also be influenced by braiding density and underlayer balloon wall thickness, but at least when these parameters are substantially fixed, the location of the hinge point will occur at higher corresponding diameters as the inflation pressure of the underlayer balloon during manufacture of the composite balloon is increased.

The intersection point may be manipulated by changing the pressure of inflation of the underlayer balloon during the manufacture of the composite balloon. Raising the inflation pressure of the underlayer balloon raises the intersection point at a given single wall of the underlayer balloon.

Underlayer Balloon

In some aspects the invention pertains to a composite balloon, or method of forming same, in which a web material is formed from fibers by application over an underlayer balloon form that becomes integrated into the composite balloon.

The underlayer balloon may be preformed in a manner known for forming medical device balloons. For instance a tubular parison of a semi-crystalline polymeric material may be radially expanded, or radially expanded with longitudinal stretching to form the underlayer balloon. Optionally the underlayer balloon may be still further processed before it is incorporated into the composite balloon. The extruded parison used to prepare the underlayer balloon may be radially expanded as is into a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison. Examples of these techniques may be found in the patent documents mentioned elsewhere in this application or in U.S. Pat. No. 4,963,313, Noddin et al., U.S. Pat. No. 5,306,246 Sahatjian, U.S. Pat. No. 4,935,190, Tennerstedt, U.S. Pat. No. 5,714,110, Wang et al., U.S. Pat. No. 5,304,340, Downey. Various known methods of altering the properties of a radially expanded balloon such as heat-setting, heat shrinking, and/or radiation crosslinking may also be employed in forming the underlayer balloon. See U.S. Pat. No. 5,403,340, Wang et al.; EP 540858, Advanced Cardiovascular Systems, Inc.; and WO 98/03218, Scimed Life Systems.

The underlayer balloon may be formed of any material which may be made by radial expansion of a tubular parison, typically thermoplastic polymers. Documents pertinent to materials which may be employed this way include U.S. Pat. No. 4,906,244, Pinchuk et al., and U.S. Pat. No. 5,328,468, Kaneko, which describe polyamide balloons; U.S. Pat. No. 4,950,239, Gahara, and U.S. Pat. No. 5,500,180, Anderson et al., which describe balloons made from polyurethane block copolymers; U.S. Pat. No. 5,556,383, Wang et al., and U.S. Pat. No. 6,146,356, Wang et al., which describe balloons made from polyether-block-amide copolymers and polyester-block-ether copolymers; U.S. Pat. No. 6,270,522, Simhambhatla, et al., which describes balloons made from polyester-block-ether copolymers of high flexural modulus; U.S.

Pat. No. 5,344,400, Kaneko, which describes balloons made from polyarylene sulfide; and U.S. Pat. No. 5,833,657, Reinhart et al., which describes balloons having a layer of polyetheretherketone. U.S. Pat. No. 5,250,069, Nobuyoshi et al., U.S. Pat. No. 5,797,877, Hamilton et al., and U.S. Pat. No. 5,270,086, Hamlin, describe still further materials which may be used to make such balloons.

Such materials may include low, linear low, medium and high density polyethylenes; polypropylenes; poly(ethylene vinyl acetate) (EVA); poly(ethylene vinyl alcohol) (EVOH) and EVA/EVOH terpolymers; polyolefin-ionomers; ethylene-butylene-styrene block copolymers blended with low molecular weight polystyrene and, optionally, polypropylene, and similar compositions substituting butadiene or isoprene in place of the ethylene and butylene; poly(vinyl chloride); polyurethanes; polyesters and copolyesters; polycarbonate; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); polyetheretherketone (PEEK) and PES (polyether sulfone). Physical blends and copolymers of such materials may also be used.

Orientable polymers are among the preferred materials for forming the underlayer balloon. Suitable orientable polymers include aromatic polyesters, especially polyethylene terephthalate (PET). PET polymers may have an initial intrinsic viscosity about 0.5 or more, for instance, 0.6-1.3. Other high strength polyester materials, such as poly(ethylene naphthalate) (PEN); and poly(butylene terephthalate) may also be used. Polyester copolymers incorporating ethylene terephthalate, ethylene naphthalate, butylene terephthalate and/or butylene naphthalate repeat units, may also be employed. Polyester copolymers such as the random copolymer made from dimethyl terephthalate dimethyl isophthalate and ethylene glycol described in U.S. Pat. No. 5,330,428 Wang, et al. may also be employed.

Examples of polyamides which may be used include nylon 6, nylon 64, nylon 66, nylon 610, nylon 610, nylon 612, nylon 46, nylon 9, nylon 10, nylon 11, nylon 12, and mixtures thereof.

The underlayer balloon may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4-butanediol chain extender. Tecothane® 1065D and 1075D are examples. Other polyurethanes that can be used include Isoplast® 301, a high strength engineering thermoplastic polyurethane, and Pellethane® 2363-75D, both sold by Dow Chemical Co. References illustrating polyurethane balloon materials include U.S. Pat. No. 4,950,239, to Gahara, U.S. Pat. No. 5,500,180 to Anderson et al., U.S. Pat. No. 6,146,356 to Wang, et al., and U.S. Pat. No. 6,572,813, to Zhang, et al.

Underlayer balloons may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

Polyamide/polyether polyesters are sold commercially under the Pebax® trademark. Examples of suitable commercially available polymers are the Pebax® 33 series polymers with hardness 60 and above, Shore D scale, especially Pebax® 6333, 7033 and 7233. These polymers are made up of nylon 12 segments and poly(tetramethylene ether) segments linked by ester groups.

It is also possible to utilize polyester/polyether segmented block copolymers. Such polymers are made up of at least two polyester segments and at least two polyether segments. The polyether segments are the same as previously described for the polyamide/polyether block copolymers useful in the invention. The polyester segments are polyesters of an aromatic dicarboxylic acid and a two to four carbon diol.

The polyether segments of the polyester/polyether segmented block copolymers are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. Examples of other polyethers which may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 150 and 2,500, preferably between 250 and 1000.

The polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids. Preferred polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

A suitable thermoplastic polyimide is described in U.S. Pat. No. 5,096,848 and is available commercially under the tradename Aurum® from Mitsui Toatsu Chemicals, Inc., of Tokyo, Japan.

Examples of liquid crystal polymers include the products Vectra® from Hoechst Celanese; Rodrun® from Unitika; LX and HX series polymers and Zenite™ polymers from DuPont; Sumikosuper™ and Ekonol™ from Sumitomo Chemical; Granlar™ from Grandmont; and Xydar® from Amoco. Suitably the liquid crystal polymer materials when employed in the underlayer balloon are blended with another thermoplastic polymer such as PET, nylon 12, or a block copolymer such as Pebax® 7033 or 7233 or Arintel® EM 740 or Hytrel 8230. The liquid crystal polymer may be present as filaments in a matrix of the blend polymer.

Alternatively, the underlayer balloon may be obtained by polymerization of a curable composition on a mold form, for instance as described in commonly owned applications US 2005-0015046 A1, and/or US 2006-0008606 A1.

The underlayer balloon is formed at a thickness which will provide a sufficiently rigid profile upon inflation to a low pressure, suitably 2-3 atm, to permit direct application of fibers thereto in a manner which forms a fiber web overlying the balloon. Preferably the underlayer balloon is substantially radially oriented or biaxially (radially and longitudinally) oriented. The underlayer balloon may have a wall thickness, single wall basis, of from about 5 µm to about 50 µm (0.0002-

0.002 inches), for instance 8 to 30 μm (0.0003-0.0012 inches), suitably about 10 to about 25 μm (0.0004-0.0010 inches).

Fiber Web

Various techniques for forming webs are known. Suitable webs may be braids, weaves, mesh, helical windings, knits or random rovings. The web may be formed of different materials, for instance if anisotropic longitudinal lengthening and diameter expansion properties are desired.

The fiber selection and the web pattern can influence the distension properties of the composite balloon. Fiber tension during application to the underlayer balloon can also affect distension of the composite balloon, especially if elastomeric fibers are employed in whole or in part. In some preferred embodiments, however, the composite balloon is substantially non-distensible in both the longitudinal and radial directions, in which case the fibers have very low elongation, and the pattern is selected to provide minimal expansion. Weaves or braids are particularly desirable web-forms in these embodiments. A circular braider may be employed to apply the fibers to the underlayer balloon.

The web pattern may provide crossing fibers at any angle. Typically at least one set of the fibers will wind helically around the circumference of the underlayer balloon. In at least some embodiments a set of longitudinal fibers is provided, running parallel to the longitudinal axis over at least a portion of the underlayer balloon. The longitudinal fibers may be inelastic. In some embodiments the longitudinal fibers are interwoven or braided into the web pattern with fibers that wind helically around the balloon, for instance, the helical fibers may cross over and under the longitudinal fibers in an individually or grouped alternating fashion to provide the weave or braid. Crossing fibers that run at several different angles may be used. For instance, longitudinal fibers may be crossed both by fibers running at 45° and at 135° thereto. In some embodiments, the braiding angle may be 68 to 70. Particularly with fiber webs produced using mechanical braiders, crossing angles that produce optimal reinforcement may not occur with optimal gap spacing between fiber crossings. Groupings of individual fibers may be employed to reduce gap spacing at any desired crossing angle. For instance, crossing groupings of 2-6 fibers by 2-6 fibers may give better results than 1×1 crossings. The groupings may have different sizes, for instance 2 (longitudinal) by 4 (45° helical) by 4 (135° helical).

The fibers may be monofilament or multifilament fibers. Any size which is suitable may be used. For example, in some embodiments, the fibers may range in size from 1 to 50 μm or in denier from 10-100. In some embodiments, the denier is from 25-50. Moreover, deviations from this size range can be achieved in some cases without departing from the invention.

Individual filaments in a multifilament fiber may have denier size less than 10, for instance from 1-5 denier. Larger filaments may also be employed in multifilament fibers. Multifilament fibers may be a blend of fibers of different materials.

The fiber material may be polyester, polyolefin, polyamide, polyurethane, liquid crystal polymer, polyimide, carbon, glass, mineral fiber or a combination thereof. Polyesters include polyethyleneterephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema,® sold by DSM Dyneema BVm Heerlen, Netherlands, Spectra® fibers, sold by Honeywell, and very high density polyethylene, and polypropylene fibers. Elastomeric fibers can be used in some cases. In some specific embodiments of the invention, the fibers are high strength materials which have a very low elongation and creep, such as aramid, liquid crystal polymer, or ultrahigh molecular weight polyethylene described in U.S. Pat. No. 5,578,374, U.S. Pat. No. 5,958,582 and/or U.S. Pat. No. 6,723,267. Fibers comprising carbon nanotubes or carbon nano-fibers may be suitable. Other carbon materials may also be suitable in some applications.

In some embodiments the fiber web may comprise multiple layers of fibers. However in other embodiments the fiber web has regions between crossings where a single fiber strand is employed to minimize the balloon profile. The strands may be manipulated to flatten as they are applied to increase the area covered by a single strand and minimize the profile of the fiber and of the overall balloon.

Friction Enhancement

To facilitate application of the web applied to the cone portion of the underlayer balloon, a friction-enhancing material may be provided at the interface between the underlayer balloon and the web, at least over the cone portion. The web fibers may be coated with a friction-enhancing material, or a layer of friction-enhancing material may be applied to at least the cone portion of the underlayer balloon before application of the web fibers, or both. The friction enhancing material may also be provided at the interface between the underlayer balloon and the web over other portions of the balloon, for instance over the waist and/or body portions.

The friction-enhancing material may be a polymer that has a higher coefficient of friction than either or the underlayer balloon and the fiber and which is high enough that the fibers do not substantially slip off or around on the cone during web formation. Coefficient of friction is suitably determined per ASTM D3702 against a polished steel surface and values of about 0.7 or higher are recommended, especially about 0.8 and higher. Exemplary materials may be rubbery elastomeric thermoplastic polymers, for instance, styrene-olefin block copolymers and acrylonitrile block copolymers. In some cases urethane-based thermoplastic elastomers, ester-based thermoplastic elastomers, olefin-based thermoplastic elastomers, and amide-based thermoplastic elastomers may be suitable. Linear low density polyethylene, very low density polyethylene, polyethylene-α-olefin copolymers or polycarbonate-urethane copolymers may be suitable in some cases.

One group of friction enhancers includes styrene-olefin thermoplastic elastomers. The styrene-olefin thermoplastic elastomer is a block copolymer having a soft segment and a hard segment within a molecule. The soft segment is a unit that is obtained from polymerization of an olefin, e.g., a polyisobutylene block, a polybutadiene block or a polyisoprene block. The component constituting the hard segment is a unit of styrene block, for example, that is obtained from a compound having one or at least two types selected from styrene and its derivatives, e.g., α.-methyl styrene, vinyl toluene, p-tertiary butyl styrene, 1,1-diphenyl ethylene and others.

Specific examples of the styrene-olefin thermoplastic elastomers include: styrene-isobutylene-styrene block copolymer (SIBS); styrene-butadiene-styrene block copolymer (SBS); styrene-ethylene-butylene-styrene block copolymer (SEBS); styrene-isoprene-styrene block copolymer (SIS); styrene-ethylene-propylene-styrene block copolymer (SEPS); styrene-ethylene-ethylene-propylene-styrene block copolymer (SEEPS structure); and modified block copolymers thereof. The content of styrene (or its derivatives) in each of the SIBS, SBS, SEBS, SIS, SEPS and SEEPS structures is preferably in a range of 10-50 wt. %, and more preferably in a range of 15-45 wt. % within the copolymer. A particular example is SIBS with about 17 wt % styrene.

A friction-enhancing coating material may also be an adhesive. For instance, the adhesive may be one that provides at least some tack during application of the fibers. The adhesive may be a pressure sensitive, hot melt, solution, dispersion or curable material. In some embodiments of the invention, the adhesive will set up further after application of the fiber to provide an adhering bond between the fibers and the balloon which is stronger than the initial tack adhesion. Partially cured radiation curable acrylate coating materials are exemplary.

The friction-enhancing coating may be applied from a solution or dispersion. In the case of a hot melt or curable adhesive, the coating may be applied neat. Suitable coating thicknesses are from about 1 to about 25 μm, for instance from about 2 μm to about 20 μm or from about 5 to about 10 μm.

Matrix

A polymeric matrix material is applied over the web and over any exposed portions of the underlayer balloon while the underlayer balloon is pressurized at a predetermined pressure. The matrix material should bind to the material that is at least partially exposed to the matrix material under the particular technique employed. The exposed material may be one or more of the web fiber material, the underlayer balloon and, if employed, the friction enhancing material. The matrix material may be the same or similar to the friction-enhancing material. The matrix material may also be the same or similar to the bulk material of the underlayer balloon, or it may be a wholly different material from both the friction-enhancing material and the underlayer balloon material. The matrix material in some embodiments is heat activatable, i.e. after application adhesive properties can be activated by heating.

The matrix material may be applied from solvent or dispersion. In some cases a curable liquid which sets up after application may be employed as matrix material. The matrix material may also be applied from the melt, for instance by spraying or extruding over the web.

Examples of matrix materials which may be employed include the styrene-olefin thermoplastic elastomers already described. Polyurethanes, for instance silicone modified polyurethanes may be employed. UV curable compositions as described in more detail in US 2006-0008606 A1 may also be employed.

A solution or dispersion or a polymer formulation having hot-melt adhesive properties, i.e. one that after drying may still be activated with heat to bond to a subsequently applied substrate, may be used.

In some embodiments the matrix material and the friction-enhancing material, in combination, also bind the filaments of the fibrous material to the underlayer balloon.

Outerlayer Balloon

The assembly of underlayer balloon, fiber web and matrix material may be covered with an outerlayer balloon. The outerlayer balloon is a thin molded balloon and may be preformed in a manner known for forming medical device balloons, for instance by any of the means described herein for forming the underlayer balloon. The materials of the outer layer balloon may be selected from the same materials already identified for the underlayer balloon. The material of the outer layer balloon may be the same or different from that of the underlayer balloon.

The outerlayer balloon is formed with an inner diameter which will receive the underlayer balloon and web matrix combination. In some embodiments, the outerlayer balloon is radially oriented or biaxially (radially and longitudinally) oriented.

The outerlayer balloon may have a wall thickness comparable to that of the underlayer balloon, i.e. on single wall basis from about 5 μm to about 50 μm (0.0002-0.002 inches), for instance from about 8 to about 30 μm (0.0004-0.0012 inches), suitably from about 10 to about 25 μm (0.0004-0.0010 inches).

Forming the Composite Balloon

The combination of the above described layers, as mentioned above, forms a composite balloon that is flexible and has high strength and a high burst pressure. In forming the composite balloon, the underlayer balloon 122 is formed and molded using a convention molding process.

One end of the underlayer is sealed and the underlayer balloon 122 is then pressurized and expanded to a predetermined pressure above ambient, or to a predetermined size above the size at ambient pressure. Size may be determined for instance by monitoring the radius or diameter for cylindrical balloons, or a shadow profile dimension for non-cylindrical balloons.

The pressure to inflate the underlayer balloon controls the intersection point of FIG. 5. Depending on each application and underlayer balloon double wall thickness, the pressure of the underlayer balloon may vary. In some embodiments, it is about 20-100 psi. In some embodiments, it is about 40-60 psi.

After pressurization, the underlayer balloon 122 optionally may then be coated with a friction enhancing material 124, such as a pressure sensitive adhesive. The fiber web 126 is then applied to the surface of the underlayer balloon 122, suitably as a braid of fibers of Spectra® or Vectran® materials, or the like. The fiber web 126 is then encased with matrix material 128. As a particular example a solution or dispersion or a polymer formulation having hot-melt adhesive properties upon drying may be used.

After any solvent is dried off, an outerlayer balloon may additionally be applied. For purposes of the present invention this is an optional step and in some cases a suitable composite balloon may be obtained without use of an overlayer or an overlayer may be applied without using an overlayer balloon. In the case of the addition of an outerlayer balloon, the assembly of the underlayer balloon 122, fiber web 126 and matrix 128 is then inserted into a previously formed outerlayer balloon 140. The outerlayer balloon 140 may be slightly larger than the underlayer balloon 122 or it may have the same dimensions. The proximal and distal waist of the outerlayer balloon 140 may be larger than those of the underlayer balloon 122 to ease insertion.

After insertion, the combination balloon is heat set at a temperature above the temperature at which the underlayer and outer layer balloons were formed. For instance if the underlayer and outer layer balloons are blown at a temperature in the range of about 90° C. to about 100° C., a heat set temperature in the range of from about 110° to about 130° may be employed, for instance about 115° C. A suitable heat set time may be from about 15 seconds to about 5 minutes, for instance about one minute. In some embodiments, where the activation temperature for the adhesive is the same as the molding temperature, the heat temperature does not have to be higher than the balloon molding temperature.

The heat set inflation pressure is suitably about the same or higher pressure than the pressure at which the underlayer balloon or the outer layer balloon, whichever was higher, for instance the range of about 40 to about 50 psi, with a target of 40 psi. During heat set the matrix material desirably is activated to adhere to the outerlayer balloon to laminate the layers together.

In general the conditions for formation of the underlayer 122 and outerlayer 140 may be substantially the same so that they will have similar behavior during heat set. However, in some cases it may be advantageous for the underlayer and outerlayer balloon to have been formed at different temperature and or pressure conditions such that the outer layer balloon shrinks slightly during heat set while the underlayer balloon remains unchanged or expands slightly. Such technique may increase the bonding pressure of the outerlayer balloon to the adhesive matrix material and assist in flattening fiber strands therebetween so to further minimize the total balloon thickness.

Although it should be understood that in some embodiments there is no further coating on the outerlayer balloon, the composite balloon may have a further coating of a lubricous material or which comprises drug, as is generally known. See, for instance U.S. Pat. No. 5,135,516, Sahatjian, et al.; U.S. Pat. No. 5,026,607, Kiezulas; U.S. Pat. No. 5,304,121, Sahatjian; U.S. Pat. No. 5,576,072, Hostettler, et al.; U.S. Pat. No. 5,503,631, Onishi et al.; U.S. Pat. No. 5,509,899, Fan et al.; U.S. Pat. No. 5,693,034, Buscemi et al.; U.S. Pat. No. 6,110,483, Whitbourne, et al.; U.S. Pat. No. 5,702,756, Zhong; U.S. Pat. No. 6,528,150, Nazarova et al.; and U.S. Pat. No. 6,673,053, Wang, et al.

Pressurization of the underlayer balloon is maintained at least until the fiber web has become fixedly bonded to the underlayer balloon and the subsequent steps will not modify that bonding. In the case where an overlayer balloon is applied the heat set step may alter such bonds and it is recommended that the pressurization be maintained until its completion of that step. In some cases where an outer layer is not applied the pressurization can be released after the drying, curing, cooling or other setting process of the matrix material is complete. In cases where an outer layer above the matrix material is applied from solution or dispersion pressurization should be maintained if the coating step has the potential of softening the matrix material, but can be released earlier if it does not.

Upon completion of the composite, the balloon may then be assembled onto a shaft, wrapped and sterilized.

The composite balloon may have a single wall thickness of about 50 to about 250 μm, suitably about 50 to about 230 μm. In some embodiments, the single wall thickness of about 50 to about 80 μm with a target at 60 μm.

Wall strengths for such balloons may be in excess of about 15,000 psi (103,421 kPa), typically at least about 18,000 psi (124,106 kPa), and in most cases in the range of about 25,000 to about 40,000 psi. Balloon diameters may range from about 1.5 to about 14 mm.

In some aspects, the invention may be optimized by altering the ratio of fiber and matrix material employed relative to the overall balloon thickness. Suitably the balloon has a fiber matrix ratio, taken as the thickness of the intermediate fiber and matrix material to the total thickness of the balloon, in the range of 0.51 to 0.73. The particulars of this optimization may be found in commonly owned U.S. application Ser. No. 11/407,576 titled HIGH PRESSURE BALLOON, filed Apr. 20, 2006, the contents of which are incorporated herein by reference in their entirety.

The following examples illustrate the invention in preliminary, non-optimized trials.

Example

Underlayer balloons were prepared by radial expansion of extruded tubes of Pebax® 7233 polymer. The underlayer balloons had an average double wall thickness in the body region of approximately 0.0014 inches, a molded diameter of approximately 8 mm and a molded body length of approximately 40 mm. The underlayer balloons were sterilized with ethylene oxide according to a conventional protocol. At this stage, three balloons were retained, unbraided, as controls for comparison purposes.

The underlayer balloons were heat-sealed at their distal end. The proximal end was connected to a pneumatic syringe and the balloon component was pressurized to 40 psi (2.7 atm).

A coating of pressure sensitive adhesive, HL-2081 from H.B. Fuller was applied to the exterior surface of the underlayer balloon by hand dipping the pressurized balloon component into a 25% solution of the adhesive in toluene, drawing the balloon component out of solution and allowing it to dry.

A braiding machine was then utilized to weave a web of fibers of 50 denier Dyneema fiber from DSM around the inflated balloon components. Speeds were adjusted as braiding progressed in a manner directed to achieve a single layer braiding with estimated 68-70 degree braiding angle. Braiding angle can be changed by braiding speed. Pressurization of the underlayer balloon was maintained during application of the fiber web.

For the matrix material, a 10% hot melt (HM 0230 from H.B. Fuller) solution in toluene was applied by again dipping the pressurized balloon component into a solution, drawing the balloon component out of solution and letting it thoroughly dry.

Overlayer balloons of Pebax® 7233 polymer were prepared in the same manner and with the same dimension as the underlayer balloons.

Some embodiments of the invention may be further characterized by the following numbered paragraphs.

1. A method for preparing composite fiber reinforced balloons for medical devices, the method comprising:
   providing a preformed underlayer balloon having a size at ambient pressure;
   expanding the preformed underlayer balloon by pressurizing the underlayer balloon to a predetermined pressure above ambient, or until it reaches a predetermined size above the ambient pressure size; and
   while the underlayer balloon remains pressurized:
      applying a web of fibers to the exterior of said underlayer balloon;
      adhering the web of fibers to the underlayer balloon; and
      encasing the web with a matrix material to form an assembly of underlayer balloon and fiber matrix.
2. A method as in paragraph 1, further comprising the steps of:
   applying an overlying layer over the encased web; and
   bonding said assembly and overlayer balloon to form said composite fiber reinforced balloon.
3. A method as in paragraph 2, the overlying layer being a preformed overlayer balloon layer of radially oriented polymer material, wherein the preformed overlayer balloon layer applied over the encased web by inserting the assembly of underlayer balloon and fiber matrix into the preformed overlayer balloon form.
4. A method as in paragraph 2, wherein the overlying layer is a coating layer.
5. A method as in paragraph 3, wherein the preformed overlayer balloon is radially oriented.
6. A method as in paragraph 3, wherein both the underlayer balloon layer and the overlayer balloon layer are biaxially oriented.
7. A method as in paragraph 3, wherein the matrix material comprises an adhesive material.
8. A method as in paragraph 3, wherein the matrix material is a thermally activatable adhesive.

9. A method as in paragraph 1, wherein the preformed underlayer balloon is radially oriented.
10. A method as in paragraph 1, wherein the fibers of said fiber web have a diameter of from 1 to 50 μm.
11. A method as in paragraph 1, wherein the fibers of said fiber web have a linear mass density in the range of from about 10 to about 100 denier.
12. A method as in paragraph 1, further comprising applying a layer of friction enhancing material to at least a cone portion of the underlayer balloon prior to applying fiber web.
13. A method as in paragraph 1, further comprising mounting the composite balloon on a catheter or probe.
14. A method as in paragraph 1, wherein the fiber material is selected from the group consisting of aramid, ultrahigh molecular weight polyolefin, liquid crystal polymer and mixtures thereof
15. A method as in paragraph 1, wherein the underlying balloon layer comprises a polymer selected from the group consisting of polyurethanes; polyesters and copolyesters; polycarbonates; polyamide/polyether block copolymers; polyester/polyether segmented block copolymers; silicone-polycarbonate copolymers; polyamides; thermoplastic polyimides; polyacetal; liquid crystal polymers, polyetheretherketone; polyether sulfone; and combinations thereof
16. A method as in paragraph 3, wherein said step of inserting the assembly of underlayer balloon and fiber matrix into the preformed overlayer balloon form, comprises inverting the overlayer balloon and then everting the overlayer balloon over said assembly.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:
1. A fiber reinforced laminate composite balloon comprising an underlying balloon layer, a fiber web disposed over the underlying balloon layer and a matrix material encasing the web, wherein the fiber reinforced laminate composite balloon is characterized by a non-linear compliance curve comprising first and second segments above a nominal inflation diameter of the balloon, the second segment taken over an inflation pressure range higher than the pressure range of the first segment and the balloon having a growth rate in the first segment that is greater than in the second segment.
2. A fiber reinforced laminate composite balloon as in claim 1, wherein the underlying balloon layer is radially oriented.
3. A fiber reinforced laminate composite balloon as in claim 1, wherein the fibers of said fiber web have a diameter of from 1 to 50 μm.
4. A fiber reinforced laminate composite balloon as in claim 1, wherein the fibers of said fiber web have a linear mass density in the range of from about 10 to about 100 denier.
5. A fiber reinforced laminate composite balloon as in claim 1, wherein the fiber material is selected from the group consisting of aramid, ultrahigh molecular weight polyolefin, liquid crystal polymer and mixtures thereof.
6. A fiber reinforced laminate composite balloon as in claim 1, wherein the underlying balloon layer comprises a polymer selected from the group consisting of polyurethanes; polyesters and copolyesters; polycarbonates; polyamide/polyether block copolymers; polyester/polyether segmented block copolymers; silicone-polycarbonate copolymers; polyamides; thermoplastic polyimides; polyacetal; liquid crystal polymers, polyetheretherketone; polyether sulfone; and combinations thereof.
7. A medical device comprising a balloon as in claim 1, mounted on a catheter or probe.
8. A fiber reinforced laminate composite balloon as in claim 1, further comprising an overlying layer of material disposed over the fiber web and matrix material.
9. A fiber reinforced laminate composite balloon as in claim 8, wherein the matrix material is a thermally activatable adhesive.
10. A fiber reinforced laminate composite balloon as in claim 8, wherein the overlying balloon layer comprises a polymer selected from the group consisting of polyurethanes; polyesters and copolyesters; polycarbonates; polyamide/polyether block copolymers; polyester/polyether segmented block copolymers; silicone-polycarbonate copolymers; polyamides; thermoplastic polyimides; polyacetal; liquid crystal polymers, polyetheretherketone; polyether sulfone; and combinations thereof.
11. A fiber reinforced laminate composite balloon as in claim 8, wherein the overlying layer is an overlying balloon layer of radially oriented polymer material.
12. A fiber reinforced laminate composite balloon as in claim 11, wherein the matrix material is adhesively bonded to the underlayer balloon layer, the fiber web and the overlying balloon layer.
13. A fiber reinforced laminate composite balloon as in claim 12, wherein both the underlying balloon layer and the overlying balloon layer are biaxially oriented.
14. A fiber reinforced laminate composite balloon as in claim 11, wherein the matrix material comprises an adhesive material.
15. A fiber reinforced laminate composite balloon as in claim 1, further comprising a layer of friction enhancing material between the underlying balloon layer and the fiber web.
16. A fiber reinforced laminate composite balloon as in claim 15 wherein the friction-enhancing material comprises an elastomeric polymer.
17. A catheter having an elongated tubular body, a balloon mounted on a distal end thereof and means for inflation of the balloon, wherein the balloon is a balloon as in claim 1.

* * * * *